(12) United States Patent
Madsen et al.

(10) Patent No.: US 8,455,549 B2
(45) Date of Patent: Jun. 4, 2013

(54) CARBONYLAMINO DERIVATIVES USEFUL FOR THE TREATMENT OF CERTAIN INFLAMMATORY DISORDERS

(75) Inventors: Lars Siim Madsen, Sorø (DK); Palle Christophersen, Ballerup (DK)

(73) Assignee: Aniona Aps, Farum (DK)

( * ) Notice: Subject to any disclaimer, the term of this patent is extended or adjusted under 35 U.S.C. 154(b) by 382 days.

(21) Appl. No.: 12/674,746

(22) PCT Filed: Aug. 21, 2008

(86) PCT No.: PCT/EP2008/060910
§ 371 (c)(1),
(2), (4) Date: Mar. 26, 2010

(87) PCT Pub. No.: WO2009/027292
PCT Pub. Date: Mar. 5, 2009

(65) Prior Publication Data
US 2011/0124735 A1    May 26, 2011

Related U.S. Application Data

(60) Provisional application No. 60/957,811, filed on Aug. 24, 207.

(30) Foreign Application Priority Data
Aug. 24, 2007   (DK) .................................. 2007 01211

(51) Int. Cl.
*A61K 31/165*    (2006.01)
*A61P 1/04*    (2006.01)

(52) U.S. Cl.
USPC .......................................... 514/617; 514/925

(58) Field of Classification Search
USPC ................................................ 514/617, 925
See application file for complete search history.

(56) References Cited

U.S. PATENT DOCUMENTS 7,208,527 B2   4/2007   Gouliaev et al.
7,429,618 B2   9/2008   Gouliaev et al.

FOREIGN PATENT DOCUMENTS

| WO | WO-97/34589 A1 | 9/1997 |
|---|---|---|
| WO | WO-97/34599 A2 | 9/1997 |
| WO | WO-00/50026 A1 | 8/2000 |
| WO | WO-01/27070 A1 | 4/2001 |
| WO | WO-01/49663 A2 | 7/2001 |
| WO | WO-03/004010 A1 | 1/2003 |
| WO | WO-03/059873 A1 | 7/2003 |
| WO | WO-2006/002850 A2 | 1/2006 |
| WO | WO-2007/075849 A2 | 7/2007 |

OTHER PUBLICATIONS

Inflammatory Disorders Definition,[online]. Hospital for Special Surgery, 2010 [retrieved on Mar. 21, 2010]. Retrieved from the Internet: <URL:http://www.hss.edu/condition-list_inflammatory-disorders.asp>, 2 pages.*
Lupus, [Online]. Mayo Clinic, 2005 [retrieved on Mar. 21,2010]. Retrieved from the Internet<http://web.archive.org/web/20051212052505/http://www.mayoclinic.com/health/lupus/DS00115>, 6 pages.*
Multiple Sclerosis, [Online]. PubMed Health, 2011 [retrieved on Mar. 21, 2010]. Retrieved from the Internet<http://www.ncbi.nlm.nih.gov/pubmedhealth/PMH0001747/>, 10 pages.*
Ulcerative colitis, [Online]. PubMed Health, 2011 [retrieved on Mar. 21, 2010]. Retrieved from the Internet<http://www.ncbi.nlm.nih.gov/pubmedhealth/PMH0001296/>, 4 pages.*
BS Jensen et al., "The $Ca^{2+}$-activated $K^+$channel of intermediate conductance: a possible target for immune suppression"; Expert opinion on therapeutic targets, 2002, vol. 6, No. 6, pp. 623-636.
Lars Siim Madsen et al., "Blockade of $Ca^{2+}$-activated $K^+$channels in T cells: an option for the treatment of multiple sclerosis?", European Journal of Immunology 2005, vol. 35, No. 4, pp. 1023-1026.
Heike Wulff et al., "Design of a potent and selective inhibitor of the intermediate-conductance $Ca^{2+}$-activated $K^+$channel, IKCa1: A potential immunosuppressant", Proceedings of the national acedemy of sciences of USA 2000, vol. 97, No. 14, pp. 8151-8156.

* cited by examiner

*Primary Examiner* — John Pak
*Assistant Examiner* — Andriae M Holt
(74) *Attorney, Agent, or Firm* — Birch, Stewart, Kolasch & Birch, LLP

(57) ABSTRACT

The present invention relates to the use of a particular group of carbonylamino derivatives for the treatment or alleviation of a disease or condition relating to certain inflammatory disorders.

1 Claim, No Drawings

CARBONYLAMINO DERIVATIVES USEFUL FOR THE TREATMENT OF CERTAIN INFLAMMATORY DISORDERS

This application is the National Phase of PCT/EP2008/060910 filed on Aug. 21, 2008, which claims priority under 35 U.S.C. 119(e) to U.S. Provisional Application No. 60/957,811 filed on Aug. 24, 2007 and under 35 U.S.C. 119(a) to Patent Application No. PA 2007 01211 filed in Denmark on Aug. 24, 2007, all of which are hereby expressly incorporated by reference into the present application.

TECHNICAL FIELD

The present invention relates to the use of a particular group of carbonylamino derivatives for the treatment or alleviation of a disease or condition relating to certain inflammatory disorders.

BACKGROUND ART

Inflammatory disorders are characterized by their systemic effects. Inflammation is the body's response to injury, infection or molecules perceived by the immune system as foreign. Clinically, inflammation is characterized by pain, redness, heat, swelling and altered function of affected tissue. Although the ability to mount an inflammatory response is essential for survival, the ability to control inflammation is also necessary for health.

Examples of chronic systemic inflammation disorders include inflammatory bowel disease (IBD), rheumatoid arthritis (RA) and multiple sclerosis (MS).

Inflammatory bowel disease (IBD) is a chronic autoimmune disease affecting the gastrointestinal tract with symptoms of abdominal pain, vomiting, diarrhea, hematochezia, and weight loss. IBD comes in two main forms, ulcerative colitis (UC) and Cohn's disease (CD). UC exclusively affects the colon and rectum, whereas CD may affect the entire gastrointestinal tract. Histologically UC is characterized by extended mucosal inflammation in contrast to CD, where deep punctuate lesions affects all layers of the intestinal wall. Initial stage IBD is currently treated medically by steroids, such as budesonide or aminosalicylates such as sulfasalazine, or by general immunosuppressants, such as azathioprine, whereas later stage severe cases require surgery, often in form of colostomy. Recently, antibodies against TNF-α have also been used clinically with some success.

Rheumatoid arthritis (RA) causes chronic inflammation of the joints and inflammation of the tissue around the joints, as well as other organs in the body. While rheumatoid arthritis is a chronic illness, patients may experience long periods without symptoms. Typically, however, rheumatoid arthritis is a progressive illness that has the potential to cause joint destruction and functional disability.

Multiple sclerosis (MS) is a debilitating chronic inflammatory disease that affects the central nervous system. Current research suggests that the illness is initiated by an autoimmune malfunction, where the body incorrectly directs certain leukocytes against proteins in the protective myelin sheath surrounding nerves in the brain and spinal cord. The result is multiple areas of scarring or sclerosis. Eventually, progressive damage can obliterate the nerve signals that control muscle coordination, strength, sensation and even vision.

WO 00/50026 describes Gardos channel antagonists (i.e. $Ca^{2+}$-activated K-channels), which inhibit the Gardos channel of erythrocytes, reduce sickle erythrocyte dehydration and/or delay the occurrence of erythrocyte sickling or deformation. However, the effect of such compounds with respect to inflammatory conditions is not reported.

WO 01/27070 describes the use of carbonylamino derivatives for treating CNS disorders relating to metabotropic glutamate receptor antagonists and/or agonists. However, the effect of such compounds with respect to inflammatory conditions is not reported.

WO 03/004010 describes a particular group of carbonylamino derivatives for the treatment or alleviation of diseases or conditions relating to immune regulation. However, the effect of such compounds with respect to inflammatory conditions is not reported.

WO 03/059873 describes certain carbonylamino derivatives useful as potassium channel modulators. However, the effect of such compounds with respect to inflammatory conditions is not reported.

SUMMARY OF THE INVENTION

The present invention relates to the use of a particular group of carbonylamino derivatives for the treatment or alleviation of a disease, disorder or condition relating to certain inflammatory conditions, in particular inflammatory bowel disease (IBD), multiple sclerosis (MS) and rheumatoid arthritis (RA).

Accordingly, in its first aspect, the invention relates to the use of a carbonylamino derivative of the general Formula I

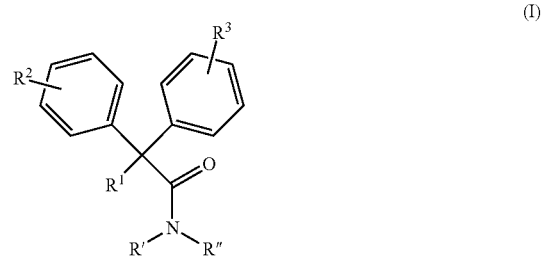

any of its enantiomers or any mixture of enantiomers, or a pharmaceutically-acceptable addition salt hereof, wherein, $R^1$ represents alkyl or phenyl, which phenyl is optionally substituted with halo or trifluoromethyl;

$R^2$ and $R^3$, independently of each other, represent hydrogen, halo or trifluoromethyl; and R' and R", independently of each other, represent hydrogen or alkyl;

for the manufacture of a medicament for the treatment, prevention or alleviation of a disease or a disorder or a condition of a mammal, including a human, which disease, disorder or condition relates to inflammatory disorders.

In another aspect the invention provides methods for the treatment, prevention or alleviation of a disease or a disorder or a condition related to inflammatory disorders, which method comprises the step of administering to such a living animal body in need thereof a therapeutically effective amount of a carbonylamino derivative as described below.

Other objects of the invention will be apparent to the person skilled in the art from the following detailed description and examples.

DETAILED DISCLOSURE OF THE INVENTION

In its first aspect the invention relates to the use of a carbonylamino derivative for the manufacture of a medicament for the treatment, prevention or alleviation of a disease or a disorder or a condition of a mammal, including a human, which disease, disorder or condition relates to immune regulation, in particular immune suppression.

The carbonylamino derivative for use according to the invention may be characterised by Formula I

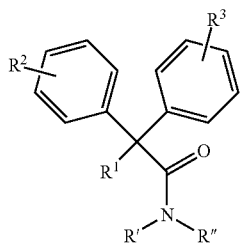

(I)

any of its enantiomers or any mixture of enantiomers, or a pharmaceutically-acceptable addition salt hereof, wherein, $R^1$ represents alkyl or phenyl, which phenyl is optionally substituted with halo or trifluoromethyl;

$R^2$ and $R^3$, independently of each other, represent hydrogen, halo or trifluoromethyl; and R' and R", independently of each other, represent hydrogen or alkyl;

for the manufacture of a medicament for the treatment, prevention or alleviation of a disease or a disorder or a condition of a mammal, including a human, which disease, disorder or condition relates to inflammatory disorders.

In a preferred embodiment the carbonylamino derivative for use according to the invention is a compound of Formula Ia

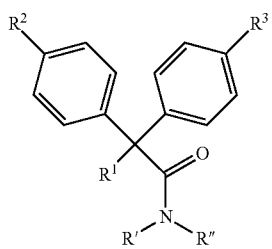

(Ia)

any of its enantiomers or any mixture of enantiomers, or a pharmaceutically-acceptable addition salt hereof, wherein $R^1$, $R^2$, $R^3$, R' and R" are as defined above.

In another preferred embodiment the carbonylamino derivative for use according to the invention is a compound of Formula Ib

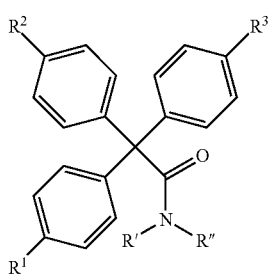

(Ib)

any of its enantiomers or any mixture of enantiomers, or a pharmaceutically-acceptable addition salt hereof, wherein $R^2$, $R^3$, R' and R" are as defined above; and
$R^4$ represents hydrogen or halo, and in particular fluoro.

In a more preferred embodiment the carbonylamino derivative for use according to the invention is a compound of Formula I, Ia or Ib, or a pharmaceutically-acceptable addition salt hereof, wherein $R^1$ represents alkyl or phenyl, which phenyl is optionally substituted with halo or trifluoromethyl.

In a more preferred embodiment, $R^1$ represents alkyl, and in particular isopropyl.

In another more preferred embodiment $R^1$ represents phenyl, which phenyl is optionally substituted with halo or trifluoromethyl.

In an even more preferred embodiment $R^1$ represents phenyl, which phenyl is optionally substituted with halo, and in particular fluoro or chloro.

In a still more preferred embodiment $R^1$ represents phenyl substituted with halo, and in particular fluoro or chloro.

In a most preferred embodiment $R^1$ represents phenyl.

In another more preferred embodiment the carbonylamino derivative for use according to the invention is a compound of Formula I, Ia or Ib, or a pharmaceutically-acceptable addition salt hereof, wherein $R^2$ and $R^3$, independently of each other, represent hydrogen, halo or trifluoromethyl.

In a more preferred embodiment, $R^2$ and $R^3$, independently of each other, represent hydrogen or halo, and in particular fluoro.

In an even more preferred embodiment, $R^2$ and $R^3$ both represent halo, and in particular fluoro.

In another more preferred embodiment, $R^2$ and $R^3$ both represent hydrogen.

In a third more preferred embodiment the carbonylamino derivative for use according to the invention is a compound of Formula I, Ia or Ib, or a pharmaceutically-acceptable addition salt hereof, wherein R' and R", independently of each other, represent hydrogen or alkyl.

In a more preferred embodiment, R' and R" both represent hydrogen.

In another more preferred embodiment, R' and R" both represent alkyl, and in particular ethyl.

In a fourth more preferred embodiment the carbonylamino derivative for use according to the invention is 2,2-Bis-(4-fluoro-phenyl)-2-phenyl-acetamide;
2,2-Bis-(4-fluoro-phenyl)-2-(2-fluoro-phenyl)-acetamide;
2,2,2-Triphenyl-acetamide;
2-(2-Fluoro-phenyl)-2,2-diphenyl-acetamide; or
2,2-Bis-(4-fluoro-phenyl)-3-methyl-butyramide;
or a pharmaceutically-acceptable addition salt hereof.

In a most preferred embodiment the carbonylamino derivative for use according to the invention is 2,2-Bis-(4-fluoro-phenyl)-2-phenyl-acetamide;
2,2-Bis-(4-fluoro-phenyl)-2-(2-fluoro-phenyl)-acetamide; or
2,2-Bis-(4-fluoro-phenyl)-3-methyl-butyramide;
or a pharmaceutically-acceptable addition salt hereof.

Definition of Substituents

In the context of this invention halo represents fluoro, chloro, bromo or iodo.

In the context of this invention an alkyl group designates a univalent saturated, straight or branched hydrocarbon chain. The hydrocarbon chain preferably contain of from one to eighteen carbon atoms ($C_{1-18}$-alkyl), more preferred of from one to six carbon atoms ($C_{1-6}$-alkyl; lower alkyl), including pentyl, isopentyl, neopentyl, hexyl and isohexyl. In a preferred embodiment alkyl represents a $C_{1-4}$-alkyl group, including butyl, isobutyl, secondary butyl, and tertiary butyl. In another preferred embodiment of this invention alkyl represents a $C_{1-3}$-alkyl group, which may in particular be methyl, ethyl, propyl or isopropyl.

Pharmaceutically Acceptable Salts

The carbonylamino derivative for use according to the invention may be provided in any form suitable for the intended administration. Suitable forms include pharmaceutically (i.e. physiologically) acceptable salts, or pre- or pro-drug forms of the carbonylamino derivative for use according to the invention.

Examples of pharmaceutically acceptable addition salts include, without limitation, the non-toxic inorganic and organic acid addition salts such as the acetate derived from acetic acid, the aconate derived from aconitic acid, the ascorbate derived from ascorbic acid, the benzenesulphonate derived from benzensulphonic acid, the benzoate derived from benzoic acid, the cinnamate derived from cinnamic acid, the citrate derived from citric acid, the embonate derived from embonic acid, the enantate derived from enanthic acid, the formate derived from formic acid, the fumarate derived from fumaric acid, the glutamate derived from glutamic acid, the glycolate derived from glycolic acid, the hydrochloride derived from hydrochloric acid, the hydrobromide derived from hydrobromic acid, the lactate derived from lactic acid, the maleate derived from maleic acid, the malonate derived from malonic acid, the mandelate derived from mandelic acid, the methanesulphonate derived from methane sulphonic acid, the naphthalene-2-sulphonate derived from naphtalene-2-sulphonic acid, the nitrate derived from nitric acid, the perchlorate derived from perchloric acid, the phosphate derived from phosphoric acid, the phthalate derived from phthalic acid, the salicylate derived from salicylic acid, the sorbate derived from sorbic acid, the stearate derived from stearic acid, the succinate derived from succinic acid, the sulphate derived from sulphuric acid, the tartrate derived from tartaric acid, the toluene-p-sulphonate derived from p-toluene sulphonic acid, and the like. Such salts may be formed by procedures well known and described in the art.

Other acids such as oxalic acid, which may not be considered pharmaceutically acceptable, may be useful in the preparation of salts useful as intermediates in obtaining a carbonylamino derivative for use according to the invention and its pharmaceutically acceptable acid addition salt.

Metal salts of a carbonylamino derivative for use according to the invention include alkali metal salts, such as the sodium salt, of a carbonylamino derivative for use according to the invention containing a carboxy group.

Steric Isomers

The carbonylamino derivatives of the present invention may exist in (+) and (−) forms as well as in racemic forms. The racemates of these isomers and the individual isomers themselves are within the scope of the present invention.

Racemic forms can be resolved into the optical antipodes by known methods and techniques. One way of separating the diastereomeric salts is by use of an optically active acid, and liberating the optically active amine compound by treatment with a base. Another method for resolving racemates into the optical antipodes is based upon chromatography on an optical active matrix. Racemic compounds of the present invention can thus be resolved into their optical antipodes, e.g., by fractional crystallisation of d- or l- (tartrates, mandelates, or camphor-sulphonate) salts for example.

The carbonylamino derivatives of the present invention may also be resolved by the formation of diastereomeric amides by reaction of the carbonylamino derivative of the present invention with an optically active activated carboxylic acid such as that derived from (+) or (−) phenylalanine, (+) or (−) phenylglycine, (+) or (−) camphanic acid or by the formation of diastereomeric carbamates by reaction of the carbonylamino derivative of the present invention with an optically active chloroformate or the like.

Additional methods for the resolving the optical isomers are known in the art. Such methods include those described by Jaques J, Collet A, & Wilen S in "*Enantiomers, Racemates, and Resolutions*", John Wiley and Sons, New York (1981).

Methods of Preparation

The carbonylamino derivatives for use according to the invention may be prepared by conventional methods for chemical synthesis, e.g. those described in WO 00/50026, WO 01/27070, WO 03/004010 and WO 03/059873.

Biological Activity

According to the present invention the carbonylamino derivatives described herein have been found particularly useful as anti-inflammatory agents, and in particular for combating inflammatory bowel disease (IBD), multiple sclerosis (MS) or rheumatoid arthritis (RA).

The inflammatory bowel disease may in particular be Crohn's disease or ulcerative colitis.

Pharmaceutical Compositions

In yet another aspect the invention relates to pharmaceutical compositions for use in the treatment or alleviation of diseases, disorders or conditions related to immune regulation, which pharmaceutical composition comprises a therapeutically effective amount of a carbonylamino derivative, as identified by the method of the invention.

While a carbonylamino derivative for use according to the invention for use in therapy may be administered in the form of the raw carbonylamino derivative, it is preferred to introduce the active ingredient, optionally in the form of a physiologically acceptable salt, in a pharmaceutical composition together with one or more adjuvants, excipients, carriers, buffers, diluents, and/or other customary pharmaceutical auxiliaries.

In a preferred embodiment, the invention provides pharmaceutical compositions comprising the carbonylamino derivative for use according to the invention or a pharmaceutically acceptable salt or derivative thereof together with one or more pharmaceutically acceptable carriers therefore and, optionally, other therapeutic and/or prophylactic ingredients. The carrier(s) must be "acceptable" in the sense of being compatible with the other ingredients of the formulation and not deleterious to the recipient thereof.

The pharmaceutical composition of the invention may be administered by any convenient route which suite the desired therapy. Preferred routes of administration include oral administration, in particular in tablet, in capsule, in dragée, in powder, or in liquid form, and parenteral administration, in particular cutaneous, subcutaneous, intramuscular, or intravenous injection. The pharmaceutical composition may be prepared by the skilled person using standard and conventional techniques appropriate to the desired formulation. When desired, compositions adapted to give sustained release of the active ingredient may be employed.

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

Further details on techniques for formulation and administration may be found in the latest edition of *Remington's Pharmaceutical Sciences* (Maack Publishing Co., Easton, Pa.).

The actual dosage depends on the nature and severity of the disease being treated, and is within the discretion of the physician, and may be varied by titration of the dosage to the particular circumstances of this invention to produce the desired therapeutic effect. However, it is presently contemplated that pharmaceutical compositions containing of from about 0.1 to about 500 mg of active ingredient per individual dose, preferably of from about 1 to about 100 mg, most preferred of from about 1 to about 10 mg, are suitable for therapeutic treatments.

The active ingredient may be administered in one or several doses per day. A satisfactory result can, in certain instances, be obtained at a dosage as low as 0.1 µg/kg i.v. and 1 µg/kg p.o. The upper limit of the dosage range is presently considered to be about 10 mg/kg i.v. and 100 mg/kg p.o. Preferred ranges are from about 0.1 µmg/kg to about 10 mg/kg/day i.v., and from about 1 µg/kg to about 100 mg/kg/day p.o.

Methods of Therapy

Viewed from another aspect, the invention provides a method for treatment, prevention or alleviation of a disease or a disorder or a condition of a living animal body, including a human, which disease, disorder or condition is related to inflammatory disorders.

In a preferred embodiment the disease, disorder or condition related to an inflammatory disorder is inflammatory bowel disease (IBD), multiple sclerosis (MS) or rheumatoid arthritis (RA).

It is at present contemplated that suitable dosage ranges are 0.1 to 1000 milligrams daily, 10-500 milligrams daily, and especially 30-100 milligrams daily, dependent as usual upon the exact mode of administration, form in which administered, the indication toward which the administration is directed, the subject involved and the body weight of the subject involved, and further the preference and experience of the physician or veterinarian in charge.

EXAMPLES

The invention is further illustrated with reference to the following examples, which are not intended to be in any way limiting to the scope of the invention as claimed.

Example 1

Inhibition of 2,4-Dinitrobenzenesulfonic Acid (DNBS)-induced Distal Colitis in Rats Test substances A and B were evaluated for possible inhibition of 2,4-Dinitrobenzenesulfonic Acid (DNBS)-induced distal colitis in rats, which is a model of inflammatory bowel disease.

Compound A, i.e. 2,2-Bis-(4-fluoro-phenyl)-3-methyl-butyramide, published as Compound 19 of WO 03/059873, was obtained essentially as described in WO 03/059873.

Compound B, i.e. 2,2-Bis-(4-fluoro-phenyl)-2-phenyl-acetamide, published to as Compound 3 in Table 1 (page 11) of WO 00/50026, was obtained essentially as described in WO 00/50026.

The test compounds were soluble in a mixture of Cremophore EL, PEG400 and distilled water (10:10:80). Test substance was administered orally (PO) twice daily for 7 consecutive days. The dosing volume used was 10 ml/kg for PO.

For test of Compound A groups of 10 Wistar derived male rats (BioLasco Taiwan) weighing 200±10 g were used.

For test of Compound B groups of 5 Wistar derived male rats (BioLasco Taiwan) weighing 210±5 g were used.

The animals were fasted for 24 hours before distal colitis was induced by intra-colonic instillation of DNBS (2,4-dinotrobenzene sulphonic acid, 30 mg in 0.5 ml 30% ethanol/ 0.9% NaCl) with a catheter of 10 cm in length, followed by gentle injection of air (2 ml) through the catheter to ensure that the solution remained in the colon. Test substance was administered orally twice daily for 7 consecutive days. The first dose was started 1 day prior to DNBS instillation. The positive standard, sulfasalazine at 300 mg/kg, was given 24 hours and 2 hours before DNBS instillation and then once daily for 5 consecutive days thereafter. One normal control group was treated without DNBS challenge. The animals were sacrificed 12 hours (bid dose) or 24 hours (sulfasalazine-treated group) after the final daily dosing and the colon was removed and weighed.

During the experiment, faecal occult blood and stool consistency were monitored daily. Furthermore, when the abdominal cavity was opened before removal of the colon, adhesions between the colon and other organs were noted. Also, the presence of colonic ulceration after removal and weighing of each colon (a macroscopic damage score) was recorded. Then each colon sample was divided lengthwise into two segments, one segment was fixed in liquid nitrogen.

The colon-to-body weight ratio was calculated according to the formula:

(A) Colon-to-Body weight ratio (Colon weight/100 g B. W.) for each rat in respective treatment groups (vehicle blank, vehicle+DNBS, Test substance+DNBS and positive reference agent+DNBS)

$$\frac{\text{Weight (g) of Dissected Colon} \times 100}{\text{Body Weight (g) on 8th day}}$$

(B) The Net Increase of Colon weight/100 g B. W.

For "vehicle+DNBS": [(vehicle+DNBS)−(vehicle blank)] mean value of colon-to-body weight ratio For "test substance+DNBS": [(test substance+DNBS)−(vehicle blank)] mean value of colon-to-body weight ratio (C) The percent decrease of colon weight/100 g B. Wt.

$$\frac{[(\text{Vehicle} + DNBS) - (\text{Test Substance} + DNBS)]}{(\text{Vehicle} + DNBS) \text{ Net Increase of Colon Wt.}/100 \text{ g } B. \text{ Wt.}} \text{ Net Increase of Colon Wt.}/100 \text{ g } B. \text{ Wt.} \times 100\%$$

A 30 percent or more (≧30%) reduction in the colon-to-body weight ratio relative to the vehicle-treated group was considered significant anti-inflammatory activity. Compound A at 0.3, 1 and 3 mg/kg caused significant inhibition (≧30% inhibition) of the DNBS-induced distal colitis relative to the vehicle group.

Sulfasalazine, the positive standard, showed significant inhibition of the DNBS-induced distal colitis (52%) following daily dosing at 300 mg/kg PO for 7 consecutive days.

The results are summarized in the table below.

| Treatment | Route | Dose | % Inhibition Relative to Vehicle | No. of rats |
|---|---|---|---|---|
| Vehicle | PO | 10 ml/kg, bid × 7 | 0 | 10 |
| Sulfasalazine | PO | 300 mg/kg × 7 | (52)* | 10 |
| Compound A | PO | 0.3 mg/kg, bid × 7 | (33)* | 10 |
|  | PO | 1 mg/kg, bid × 7 | (54)* | 10 |
|  | PO | 3 mg/kg, bid × 7 | (61)* | 10 |
| Compound B | PO | 3 mg/kg, bid × 7 | (39) | 5 |
|  | PO | 30 mg/kg, bid × 7 | (57)* | 5 |

The results were evaluated in two ways:

(1) In accordance with in-house established criteria, a 30 percent or more ($\geq$30%) inhibition of the DNBS-induced distal colitis relative to the vehicle group (in parenthesis).

(2)*P<0.05 vs. vehicle control; ANOVA followed by Dunnett's test.

It is concluded that Compound A in doses of 0.3, 1 and 3 mg/kg PO caused significant inhibition of the DNBS-induced colitis in rats.

Compound B (3 and 30 mg/kg) caused significant inhibition of the increase in colon weight in DNBS-induced colitis, indicating anti-inflammatory activity ($\geq$30% inhibition vs. vehicle control [Cremophore EL/PEG400/D.W. (10:10:80)]).

The results were also evaluated by using One-way ANOVA followed by Dunnett's test. Compound B at 30 mg/kg exhibited statistically significant anti-inflammatory activity relative to the vehicle control (P<0.05).

In addition, Compound A and Compound B were associated with improved stool consistency, occult faecal blood and macroscopic damage (adhesion and ulcers in some cases) in the colon.

The invention claimed is:

1. A method for the treatment or alleviation of an inflammatory bowel disease selected from the group consisting of ulcerative colitis and Crohn's disease, which method comprises the step of administering to a living animal body in need thereof a therapeutically effective amount ranging from 0.3 mg/kg to 3 mg/kg of 2,2-bis-(4-fluorophenyl)-3-methyl-butyramide or a pharmaceutically-acceptable addition salt thereof.

* * * * *